United States Patent
Tatsuguchi et al.

(10) Patent No.: US 9,642,792 B2
(45) Date of Patent: May 9, 2017

(54) W/O/W EMULSION HAVING TEMPORAL STABILITY AND METHOD FOR PRODUCING THE SAME

(71) Applicant: SUNTORY HOLDINGS LIMITED, Osaka-shi, Osaka (JP)

(72) Inventors: Iwao Tatsuguchi, Osaka (JP); Tatsuo Matsuoka, Osaka (JP)

(73) Assignee: SUNTORY HOLDINGS LIMITED, Osaka-shi, Osaka (JP)

( * ) Notice: Subject to any disclaimer, the term of this patent is extended or adjusted under 35 U.S.C. 154(b) by 0 days.

(21) Appl. No.: 14/376,150

(22) PCT Filed: Feb. 27, 2013

(86) PCT No.: PCT/JP2013/055166
§ 371 (c)(1),
(2) Date: Aug. 1, 2014

(87) PCT Pub. No.: WO2013/129482
PCT Pub. Date: Sep. 6, 2013

(65) Prior Publication Data
US 2014/0378417 A1  Dec. 25, 2014

(30) Foreign Application Priority Data

Feb. 28, 2012 (JP) .................... 2012-041959

(51) Int. Cl.
| | | |
|---|---|---|
| A61K 8/92 | (2006.01) |
| A61K 8/891 | (2006.01) |
| A61K 8/23 | (2006.01) |
| A61Q 19/00 | (2006.01) |
| A61K 8/894 | (2006.01) |
| A61K 8/55 | (2006.01) |
| A61K 8/49 | (2006.01) |
| A61K 8/67 | (2006.01) |
| A61K 8/31 | (2006.01) |
| A61K 8/81 | (2006.01) |
| A61K 8/06 | (2006.01) |
| A61K 8/73 | (2006.01) |
| A61K 8/893 | (2006.01) |

(52) U.S. Cl.
CPC ............ *A61K 8/92* (2013.01); *A61K 8/066* (2013.01); *A61K 8/23* (2013.01); *A61K 8/31* (2013.01); *A61K 8/498* (2013.01); *A61K 8/55* (2013.01); *A61K 8/676* (2013.01); *A61K 8/678* (2013.01); *A61K 8/73* (2013.01); *A61K 8/8152* (2013.01); *A61K 8/891* (2013.01); *A61K 8/893* (2013.01); *A61K 8/894* (2013.01); *A61K 8/922* (2013.01); *A61K 8/927* (2013.01); *A61Q 19/00* (2013.01); *A61K 2800/52* (2013.01); *A61K 2800/592* (2013.01)

(58) Field of Classification Search
None
See application file for complete search history.

(56) References Cited

U.S. PATENT DOCUMENTS

| | | | |
|---|---|---|---|
| 5,567,426 A | 10/1996 | Nadaud et al. | |
| 5,798,108 A | 8/1998 | Nadaud et al. | |
| 5,955,003 A * | 9/1999 | Terren | A61K 8/06 424/401 |
| 6,290,943 B1 | 9/2001 | Naser et al. | |
| 6,387,874 B1 * | 5/2002 | Schalitz | C11D 1/62 510/199 |
| 7,427,412 B1 * | 9/2008 | Painter | A61K 8/0208 424/443 |
| 2004/0091449 A1 * | 5/2004 | Lin | A61K 8/97 424/74 |
| 2004/0137019 A1 | 7/2004 | Nakamura et al. | |
| 2007/0231279 A1 * | 10/2007 | Schulz | A61K 8/35 424/59 |
| 2009/0232856 A1 * | 9/2009 | Patel | A61K 8/066 424/401 |
| 2012/0201905 A1 | 8/2012 | Mune et al. | |
| 2013/0216665 A1 * | 8/2013 | Mason | A23L 1/27 426/250 |

FOREIGN PATENT DOCUMENTS

| | | | | |
|---|---|---|---|---|
| FR | WO 2012059590 A1 * | 5/2012 | | A23L 1/27 |
| JP | H07-51561 A | 2/1995 | | |
| JP | H07-509177 A | 10/1995 | | |
| JP | H08-501488 A | 2/1996 | | |

(Continued)

OTHER PUBLICATIONS

Masayoshi Nagai, et al., "Advances and prospective problems of complex phase emulsion," Fragrance Journal, 1989, vol. 4, pp. 88-93.
Office Action dated Oct. 22, 2013 of the corresponding Japanese Application No. 2013-538396.
Office Action dated Feb. 13, 2014 of the corresponding Japanese Application No. 2013-538396.
Office Action dated Jan. 27, 2014 of the corresponding Taiwan Application No. 102106944.

(Continued)

*Primary Examiner* — Robert A Wax
*Assistant Examiner* — Caralynne Helm
(74) *Attorney, Agent, or Firm* — Drinker Biddle & Reath LLP

(57) ABSTRACT

An object of the present invention is to provide a W/O/W emulsion having temporal stability, which comprises a water soluble active component in an inner aqueous phase, and a method for producing the same. This invention makes it possible to provide a W/O/W emulsion having temporal stability by incorporating a water soluble active component in an inner aqueous phase, a solid oil component and a silicone surfactant in an oil phase, and a water soluble polymer in an outer aqueous phase.

15 Claims, 2 Drawing Sheets

(56) References Cited

FOREIGN PATENT DOCUMENTS

| JP | H08-245364 A | 9/1996 |
|---|---|---|
| JP | 2002-275029 A | 9/2002 |
| JP | 2003-511235 A | 3/2003 |
| JP | 2003-104861 A | 4/2003 |
| JP | 2004-307414 A | 11/2004 |
| JP | 2007-519506 A | 7/2007 |
| JP | 2011-178972 A | 9/2011 |
| KR | 20030049558 A | 6/2003 |
| WO | WO-2005/049189 A1 | 6/2005 |
| WO | WO-2011/001781 A1 | 1/2011 |
| WO | WO-2011065771 A2 | 6/2011 |

OTHER PUBLICATIONS

International Search Report mailed May 14, 2013 for PCT/JP2013/055166.

EP Application 13754399.7—Extended European Search Report mailed Nov. 3, 2015.

\* cited by examiner

W/O/W EMULSION HAVING TEMPORAL STABILITY AND METHOD FOR PRODUCING THE SAME

CROSS REFERENCE TO RELATED APPLICATIONS

This application is the National Stage of International Application No. PCT/JP2013/055166, filed Feb. 27, 2013, and claims benefit of Japanese Application No. 2012-041959, filed on Feb. 28, 2012.

TECHNICAL FIELD

The present invention relates to a W/O/W emulsion and a method for producing the same. More particularly, the present invention relates to a W/O/W emulsion having temporal stability which comprises a water soluble active component in an inner aqueous phase, and a method for producing the same.

BACKGROUND ART

Water-in-oil-in-water (W/O/W) emulsions, which are multiphase emulsions having water-in-oil (W/O) droplets dispersed in their outer aqueous phase, are known as a formulation technique that can improve the percutaneous absorbability of active components as compared with other emulsion types (Non-patent Document 1), and are expected to find use in various applications including cosmetics, foods, and pharmaceuticals.

It is generally known that W/O/W emulsions are thermodynamically unstable systems so that when left standing for a long time, they are resolved or broken by creaming or flocculation followed by coalescence, whereupon they can no longer revert to the original stable emulsions.

In order to address this tendency, various attempts have been made to stabilize W/O/W emulsions. For example, the following methods have been known: a method for producing a W/O/W emulsion comprising an ascorbic acid derivative as an active component, in which a W/O emulsion having a water soluble active component dispersed in an inner aqueous phase is prepared using a dextrin fatty acid ester, and then dispersed and emulsified in an outer aqueous phase comprising an acrylic acid/alkyl methacrylate copolymer (Patent Document 1); and a method for producing a W/O/W emulsion, in which an electrolyte is added to an inner aqueous phase, the mixture is emulsified using a specified emulsifier to prepare a W/O emulsion, and the resulting emulsion is dispersed in an outer aqueous phase comprising an alkyl-modified carboxyvinyl polymer (Patent Document 2).

Meanwhile, since cosmetics are exposed to extremely harsh conditions in the stages of distribution and consumption among users, there has been a need to conduct stability investigations from more diverse perspectives, including change in properties of cosmetic products and chemical change in the active components to be incorporated. Further, the greatest interest among consumers is the usefulness of cosmetic products; thus, in the process of developing cosmetic products, the requirements for usability (e.g., impression from use, ease of use, preference) and functionality (e.g., moisture retention, skin lightening, prevention of skin roughness, anti-aging) need to be satisfied.

CITATION LIST

Patent Documents

Patent Document 1: Japanese Patent Application Publication No. JP 2004-307414 (Japanese Patent No. JP 4282358)
Patent Document 2: Japanese Patent Application Publication No. JP 2002-275029 (Japanese Patent No. JP 4601031)

Non-Patent Documents

Non-patent Document 1: FRAGRANCE JOURNAL, 1989, no. 4, p. 88-93

SUMMARY OF INVENTION

Technical Problem

In the field of cosmetics, there is a need for a W/O/W emulsion that is of sufficiently good quality to satisfy the requirements for various factors including stability and usefulness. To be specific, it is expected to develop a technique for improving the temporal stability of a W/O/W emulsion, and the stability and skin permeability of an active component having a skin-lightening effect and the like.

Thus, an object of the present invention is to provide a W/O/W emulsion having temporal stability, which comprises a water soluble active component in an inner aqueous phase, and a method for producing the same.

Solution to Problem

As a result of extensive studies, the present inventors have found that a W/O/W emulsion is stabilized by incorporating a solid oil component and a silicone surfactant in an oil phase, and a water soluble polymer in an outer aqueous phase. Through the use of this technique, the inventors have completed the present invention relating to a W/O/W emulsion having temporal stability, which comprises a water soluble active component in an inner aqueous phase.

More specifically, the present invention relates to, but is not limited to, the following W/O/W emulsion and the following method for producing the same.

(1) A W/O/W emulsion comprising: a water soluble active component in an inner aqueous phase; a solid oil component and a silicone surfactant in an oil phase; and a water soluble polymer in an outer aqueous phase.

(2) The W/O/W emulsion according to (1), wherein the silicone surfactant has a polyether group and an alkyl group.

(3) The W/O/W emulsion according to (2), wherein the silicone surfactant having a polyether group and an alkyl group is lauryl PEG-9 polydimethylsiloxyethyl dimethicone or cetyl PEG/PPG-10/1 dimethicone.

(4) The W/O/W emulsion according to any one of (1) to (3), wherein a HLB value of the silicone surfactant is 7 or less.

(5) The W/O/W emulsion according to any one of (1) to (4), wherein the content of the solid oil component is 0.7% by weight or more.

(6) The W/O/W emulsion according to any one of (1) to (5), wherein the solid oil component is a wax.

(7) The W/O/W emulsion according to any one of (1) to (6), wherein the water soluble polymer is an acrylic acid/alkyl methacrylate copolymer or xanthan gum.

(8) The W/O/W emulsion according to any one of (1) to (7), further comprising a metal salt in the inner aqueous phase.

(9) The W/O/W emulsion according to any one of (1) to (8), wherein the water soluble active component is an ascorbic acid derivative.

(10) The W/O/W emulsion according to any one of (1) to (9), wherein the weight ratio of the inner aqueous phase to the oil phase is in the range of 10:90 to 90:10.

(11) The W/O/W emulsion according to any one of (1) to (10), further comprising an oil soluble active component in the oil phase.

(12) The W/O/W emulsion according to any one of (1) to (11), wherein the oil soluble active component is a tocopherol derivative.

(13) The W/O/W emulsion according to any one of (1) to (12), wherein the W/O/W emulsion is a skin preparation for external use.

(14) A method for producing a W/O/W emulsion, comprising the steps of:

mixing and emulsifying an inner aqueous phase comprising a water soluble active component and an oil phase comprising a solid oil component and a silicone surfactant to thereby prepare a W/O emulsion; and mixing and emulsifying the prepared W/O emulsion and an outer aqueous phase comprising a water soluble polymer.

(15) The method according to (14), wherein the inner aqueous phase and the oil phase are mixed at a weight ratio of 10:90 to 90:10.

Advantageous Effects of Invention

The present invention provides a W/O/W emulsion having temporal stability, which comprises a water soluble active component in an inner aqueous phase, and a method for producing the same. The W/O/W emulsion of this invention can be applied to techniques for formulating cosmetics having various functions including skin-lightening effect.

DESCRIPTION OF EMBODIMENTS

Figure 1:
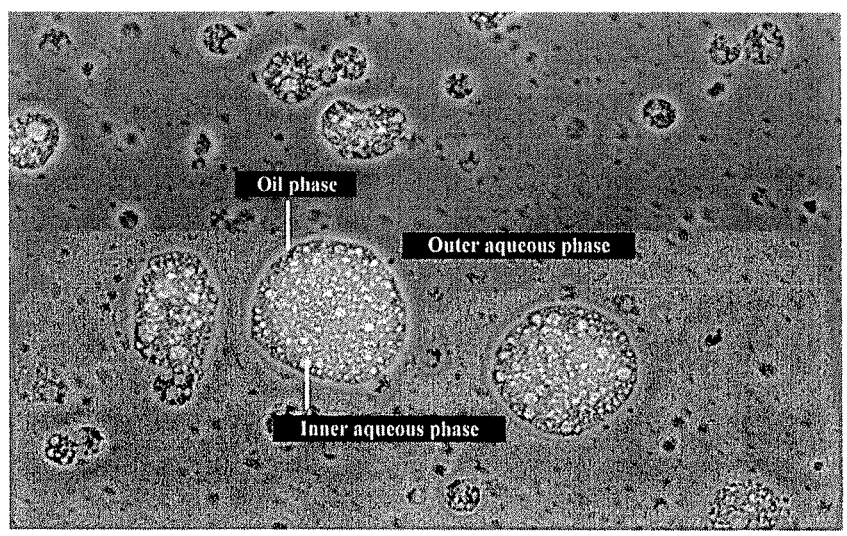
FIG. 1 shows an optical microphotograph (×400) of W/O/W emulsion (1) which is an embodiment of the present invention.

Next, various embodiments of the present invention will be described by way of examples.

W/O/W Emulsion

The W/O/W emulsion of the present invention is a W/O/W emulsion comprising: a water soluble active component in an inner aqueous phase; a solid oil component and a silicone surfactant in an oil phase; and a water soluble polymer in an outer aqueous phase. Since the W/O/W emulsion of this invention is superior in stability and has long-term storage stability, the W/O/W emulsion is particularly useful in various fields including cosmetics.

The specific components of a W/O/W emulsion which is an embodiment of the present invention are as described below. As used in the present invention, the terms "inner aqueous phase," "oil phase," and "outer aqueous phase" can either mean respective phases of a W/O/W emulsion, or respective solutions containing respective phase components to be used for producing a W/O/W emulsion.

<Inner Aqueous Phase Component>

Examples of the inner aqueous phase component that can be incorporated include, but are not particularly limited to, various water soluble active components. The water soluble active components include those components like ascorbic acid derivatives which have a viscosity-reducing effect, and such components generally make a W/O/W emulsion unstable. However, the present invention adopts multiple techniques for stabilizing a W/O/W emulsion, so that storage stability can be maintained irrespective of the type of an active component.

Examples of the water soluble active components used in the present invention include known skin-lightening components such as ascorbic acid derivatives (vitamin C derivatives), arbutin, ellagic acid, Chamomile ET, t-AMCHA, tranexamic acid, placenta extract, linolic acid, lucinol, hydroquinone, and astaxanthin. Other examples include anti-aging components, plant extracts, and other beautifying components, which will be exemplified below.

The ascorbic acid derivatives which are one type of the water soluble active components are not particularly limited as long as they are those derivatives which are generally known in the field of cosmetics, and preferred examples include ascorbic acid phosphate ester, ascorbic acid glucoside, and salts thereof, and ascorbic acid glycoside, with magnesium ascorbyl phosphate being particularly preferred.

The content of the water soluble active component is not particularly limited, and is for example in the range of 0.0001 to 50% by weight, preferably in the range of 0.005 to 20% by weight, more preferably in the range of 0.001 to 10% by weight.

Further, a metal salt such as magnesium sulfate may be contained as an additional inner aqueous phase component. The metal salt is not particularly limited, and preferred examples include magnesium sulfate, sodium citrate, amino acid salts (e.g., sodium glutamate), sodium lactate, and sodium chloride, with magnesium sulfate being particularly preferred. The content of the metal salt is not particularly limited, and is for example in the range of 0.001 to 50% by weight, preferably in the range of 0.01 to 10% by weight, more preferably in the range of 0.1 to 5% by weight.

<Oil Phase Components>

Incorporation of a solid oil component as an oil phase component can increase the viscosity of the oil phase to reduce the flowability of an inner aqueous phase. The solid oil component is not particularly limited, and is selected from solid oils and fats, waxes, hydrocarbons, higher fatty acids, higher alcohols, esters, silicones, and the like, with solid oils and fats, and waxes being particularly preferred. The solid oils and fats can be exemplified by cacao butter, coconut oil, palm oil, palm kernel oil, hydrogenated oil, hydrogenated castor oil, Japan wax, and shea butter. The waxes can be exemplified by microcrystalline wax, beeswax, carnauba wax, candelilla wax, lanoline, and jojoba oil, with microcrystalline wax being particularly preferred.

The content of the solid oil component is not particularly limited, and is for example in the range of 0.001 to 50% by weight, preferably in the range of 0.01 to 50% by weight, more preferably in the range of 0.1 to 50% by weight. However, in the case of using a wax as the solid oil component, the content of this component is in the range of 0.001 to 50% by weight, preferably in the range of 0.01 to 10% by weight, more preferably in the range of 0.1 to 5% by weight.

The silicone surfactant which is one of the oil phase components of the present invention refers to a surfactant having a structure in which a hydrophilic substituent is introduced in silicone, and various surfactants suitable for different applications can be obtained by changing the type of the hydrophilic substituent. In the present invention, the silicone surfactant is not particularly limited; for example, it is preferably a polyether-modified silicone surfactant which uses a polyether as the substituent, and is more preferably a silicone surfactant having a polyether group and an alkyl group. The silicone surfactant having a polyether group can be exemplified by PEG-11 methyl ether dimethicone, PEG/PPG-20/22 butyl ether dimethicone, PEG-9 dimethicone, PEG-3 dimethicone, PEG-9 methyl ether dimethicone, PEG-10 dimethicone, PEG-32 methyl ether dimethicone, polysilicone-13, PEG-9 polydimethylsiloxyethyl dimethicone, PEG/PPG-19/19 dimethicone, dimethicone/PEG-10/15 crosspolymer, cetyl PEG/PPG-10/1 dimethicone, and lauryl PEG-9 polydimethylsiloxyethyl dimethicone. The silicone surfactant having a polyether group and an alkyl group can be exemplified by lauryl or cetyl dimethicone copolyols, and particular examples include cetyl PEG/PPG-10/1 dimethicone and lauryl PEG-9 polydimethylsiloxyethyl dimethicone. The above-mentioned silicone surfactants can also be used in combination.

The silicone surfactant has a HLB value of preferably 7 or less, more preferably 6 or less, still more preferably 2.5 to 5.5. The content of the silicone surfactant is for example in the range of 0.1 to 15.0% by weight, preferably in the range of 0.5 to 12.5% by weight, more preferably in the range of 1.0 to 10.0% by weight.

Also, an oil soluble active component may be contained as an optional oil phase component, and the type of this component is not particularly limited. Incorporation of the oil soluble active component in addition to the water soluble active component enables production of a cosmetic product having functions derived from the water soluble active component and those derived from the oil soluble active component at the same time. Other examples of the oil soluble active component that may be contained in the W/O/W emulsion of the present invention include anti-aging components, plant extracts, and other beautifying components, which will be exemplified below.

For example, incorporation of a tocopherol derivative (vitamin E derivative) can add blood circulation promoting, anti-oxidant, and skin softening effects to the W/O/W emulsion. The content of the oil soluble active component is for example in the range of 0.0001 to 50% by weight, preferably in the range of 0.0005 to 20% by weight, more preferably in the range of 0.001 to 10% by weight.

<Outer Aqueous Phase Component>

A water soluble polymer known as a thickening agent is contained as an outer aqueous phase component. The water soluble polymer is effective for preventing flocculation of W/O emulsion droplets because it increases the viscosity of the outer aqueous phase to reduce the flowability of the W/O emulsion.

The water soluble polymer used in the present invention is not particularly limited, and any known water soluble polymer can be used, such as natural water soluble polymers, semi-synthetic water soluble polymers, and synthetic water soluble polymers. Examples of the natural water soluble polymers include plant-based polymers such as gum Arabic, guar gum, carrageenan, pectin, agar, quince seed, starches (e.g., rice, corn, potato, wheat), and glycyrrhizinic acid; microbial polymers such as xanthan gum, dextran, and pullulan; and animal-based polymers such as collagen, casein, albumin, and gelatin. Examples of the semi-synthetic water soluble polymers include starch polymers such as carboxymethyl starch and methylhydroxypropyl starch; cellulosic polymers such as methylcellulose, nitrocellulose, ethylcellulose, hydroxyethylcellulose, hydroxypropylcellulose, sodium carboxymethylcellulose (CMC), crystalline celluloses, and cellulose powders; and alginic acid polymers such as sodium alginate and propylene glycol esters of alginic acid. Examples of the synthetic water soluble polymers include vinyl polymers such as polyvinyl alcohols, polyvinyl methyl ethers, and carboxyvinyl polymers (carbomers); polyoxyethylene polymers such as polyethylene glycols (MW 1500, 4000, 6000); copolymerized polymers such as polyoxyethylene/polyoxypropylene copolymers; acrylic polymers such as sodium polyacrylate, polyacrylamides, and acrylic acid/alkyl methacrylate copolymers; as well as polyethyleneimine, and cationic polymers. The W/O/W emulsion of this invention preferably contains an acrylic acid/alkyl methacrylate copolymer or xanthan gum. The acrylic acid/alkyl methacrylate copolymer is not particularly limited, but it is preferred that said copolymer have a molecular weight of 500000 to 3000000 and contain 10 to 30 carbon atoms in the alkyl group. The content of the water soluble polymer is for example in the range of 0.001 to 50% by weight, preferably in the range of 0.005 to 20% by weight, more preferably in the range of 0.01 to 10% by weight.

Other components to be incorporated in the outer aqueous phase are not particularly limited, and any component known to contribute to the stability of emulsions can be contained, for example, a polyoxyethylene activator can be further contained. The polyoxyethylene activator is not particularly limited, and polyoxyethylene sorbitan monooleate or the like can be used. The content of the polyoxyethylene activator is for example in the range of 0.01 to 50% by weight, preferably in the range of 0.1 to 20% by weight, more preferably in the range of 1 to 10% by weight.

<Other Components>

In addition to the components described above, the W/O/W emulsion of the present invention may contain, as appropriate, various components generally used in cosmetics, quasi-drugs, medicines, and the like, including water, oil components, emulsifiers, humectants, thickening agents, active components, antiseptic agents, pigments, powders, pH adjustors, ultraviolet absorbers, anti-oxidants, and perfumes.

As mentioned above, the W/O/W emulsion of the present invention may contain an anti-aging component, a plant extract, or any other beautifying component as a water soluble active component and/or an oil soluble active component.

Examples of the anti-aging component include collagen, hyaluronic acid, elastin, proteoglycan, ceramide, placenta, astaxanthin, polyphenols, yeast, and amino acids. The anti-aging component may be contained in any of the inner aqueous phase, the oil phase, and the outer aqueous phase, but collagen, hyaluronic acid, elastin, proteoglycan, placenta, polyphenols, yeast, or amino acids is/are preferably incorporated in the inner aqueous phase, and ceramide or astaxanthin is preferably incorporated in the oil phase.

Examples of the plant extract include *Persicaria tinctoria* (*Persicaria tinctoria* leaf), *Vitis vinifera*, *Rehmannia glutinosa*, *Cannabis sativa* (Mashiningan), *Angelica keiskei*, *Phaseolus angularis*, *Malpighia emarginata*, *Uncaria gambir*, *Persea americana*, *Linum usitatissimum*, *Hydrangea macrophylla* var. *thunbergii*, *Gynostemma pentaphyllum*, *Althaea*, *Arnica montana*, *Aloe*, *Aloe vera*, *Prunus armeniaca* var. *ansu*/*Prunus armeniaca* var. *typica*, *Fragaria*, *Ficus carica* or its leaf, *Ginkgo biloba* (*Ginkgo biloba* leaf/nut), *Oryza sativa* seed or seed coat, *Urtica thunbergiana*, *Cananga odorata*, *Curcuma longa*, *Malva sylvestris*, *Althaea officinalis*, *Prunella vulgaris* subsp. *asiatica*, *Prunus mume* (*Prunus mume* fruit) or its pulp, oolong, *Citrus unshiu* (*Citrus unshiu* peel), *Eleutherococcus senticosus*, *Rubus idaeus* subsp. *melanolasius*, *Flammulina velutipes*, *Senna obtusifolia*, *Sambucus nigra* fruit, *Styphnolobium japonicum* (sophora flower, sophora bud), *Astragalus membranaceus*, *Coptis japonica*, *Plantago asiatica* (*Plantago asiatica* seed/leaf), *Crataegus pinnatifida*/*Crataegus cuneata*, *Agave filifera* var. *compacta*, *Hordeum vulgare*, *Abelmoschus esculentus* fruit, *Panax ginseng*/*Panax* (ginseng), *Hypericum erectum*/*Hypericum perforatum* var. *angustifolium*/*Hypericum perforatum*, *Lamium album* var. *barbatum*, *Juglans mandshurica* var. *sachalinensis*, *Lilium lancifolium*/*Lilium japonicum*/*Lilium brownii* var. *corchesteri* (*Lilium lancifolium*), *Ononis*, *Ulmus laciniata*, *Fragaria ananassa*, *Nasturtium officinale* (cresson), *Petroselium crispum*, *Apium graveolens* var. *dulce*, *Olea europaea*, *Origanum vulgare*, *Citrus sinensis* fruit or peel, *Rehmannia glutinosa* var. *hueichingensis* (*Rehmannia* root), *Theobroma cacao* seed, *Diospyros kaki* or its leaf (dried calyx of *Diospyros kaki*), *Curcuma zedoaria* Roscoe, *Quercus dentata* (*Quercus dentata* tree/leaf), *Betula* or *Betura pendula*, *Cucurbita*, *Typha latifolia*, *Matricaria recutitalAnthemis nobilis*, *Paullinia cupana* seed, *Chaenomeles sinensis*, *Garcinia cambogia*, *Salix gracilistyla*, *Trametes versicolor*, *Artemisia capillaris*, *Glycyrrhiza uralensis*, *Agave cantala*, *Tussilago farfara*, *Canna generalis*, *Rubus*, *Actinidia deliciosa* fruit, *Chrysanthemum morifolium* (*Chrysanthemum morifolium* flower), *Catalpa ovata*, *Rumex japonicus*, *Citrus aurantium*, *Hedera rhombea*, *Aloe arborescens*, *Satureja hortensis*, *Cinchona*, *Cinchona succirubra*, *Brassica oleracea* var. *capitata*, unripe fruit of *Brassica oleracea* var. *capitata*, *Cucumis sativus*, *Fortunella* fruit, *Piper betle*, *Psidium guajava* fruit, *Parthenium argentatum*, *Quercus infectoria* (gallnut), *Aleurites moluccanus*, *Lycium chinense* (*Lycium chinense* fruit/leaf/root bark), *Pueraria lobata* (*Pueraria lobata* root), *Cinnamomum camphora*, *Ribes uvacrispa* fruit, *Gardenia jasminoides*, *Sasa veitchii*, *Verbena officinalis*, *Sophora flavescens*, *Vaccinium macrocarpon* fruit, *Castanea crenata* or its astringent skin, *Citrus paradisi*, *Isodon trichocarpus*, *Alpinia zerumbet* (*Alpinia zerumbet* leaf), *Laurus nobilis*, *Gentiana lutea*, *Gentiana lutea* rhizome/root, *Camellia sinensis*, *Scutellaria baicalensis* (*Scutellaria* root), *Vaccinium vitis-idaea*, *Piper nigrum*, *Coffea arabica* bean, *Arctium lappa* (*Arctium* seed), *Sesamum indicum*, *Scrophulariaceae* Juss., *Schisandra chinensis*, *Triticum aestivum*, *Oryza sativa*/*Oryza sativa* bran (red/white bran)/*Oryza sativa* oil/hydrolyzed *Oryza sativa* extract, *Amorphophallus konjac*, leaf/flower/fruit/bark of *Prunus* (*Prunus Iannesiana* var. *speciosa*, *Prunus jamasakura*, *Prunus sargentii*, *Prunus pendula* f. *ascendens*, *Prunus incisa*, *Prunus maximowiczii*, *Prunus yedoensis*, *Prunus nipponica*, *Prunus verecunda*, *Prunus apetala*, *Prunus subhirtella*, *Prunus lannesiana*, and *Prunus kanzakura*), *Prunus avium*, *Punica granatum*, *Ipomoea batatas*, *Saccharum officinarum*, *Beta vulgaris* ssp. *vulgaris*, *Salvia* (*Salvia officinalis*), *Zanthoxylum*, *Butyrospermum parkii*, *Lentinula edodes*, *Aster tataricus*, *Perilla frutescens*/*Perilla frutescens* var. *crispa* f. *viridis*/*Perilla frutescens* var. *crispa* f. *crispa*/*Perilla frutescens* var. *crispa* 'Discolor' (*Perilla frutescens* leaf/seed), *Tilia japonica*, *Lyophyllum decastes*, *Hypsizygus marmoreus*, *Hypsizygus ulmarius*, *Filipendula*, *Solanum tuberosum*, *Paeonia lactiflora*, *Paeonia lactiflora* root, *Zingiber officinale*, *Acous calamus* (*Acous calamus* root), *Iris florentina*, flower of *Cymbararia muralis* f. *alba*, *Citrullus lanatus*, *Lonicera japonica*, *Stevia rebaudiana*, *Fragaria* fruit, *Equisetum arvense*, *Stevia rebaudiana*, *Prunus salicina* fruit, *Pinus sylvestris* cone, *Larix decidua*, *Hedera helix*, *Juglans regia*, *Crataegus oxyacantha*, *Taraxacum officinale*, *Aesculus hippocastanum* (horse-chestnut), *Pyrus communis* (*Pyrus communis* fruit/branch), *Filipendula ulmaria*, *Achillea millefolium* (milfoil), *Rosa centifolia*, *Mentha piperita*/*Melissa officinalis*, *Malva sylvestris* var. *mauritiana*, *Oenanthe javanica*, *Apium graveolens*, *Cnidium officinale*, *Swertia japonica*, *Fagopyrum esculentum* seed, *Rheum palmatum*, *Raphanus sativus*, *Glycine max*, *Citrus aurantium* (*Citrus aurantium* peel/fruit), *Thymus vulgaris* (*Thymus quinquecostatus*), *Rosa Damascena* (*Rosa Damascena* flower), *Allium cepa*, *Magnolia salicifolia* (*Magnolia kobus*), *Aralia elata* or its root bark, *Salvia miltiorrhiza*, *Taraxacum hondoense* or *Taraxacum albidum*/*Taraxacum mongolicum*, *Prunus avium* fruit, *Panax ginseng* (ginseng), *Oenothera tetraptera*, *Camellia japonica*, *Centella asiatica*, *Commelina communis*, *Vigna umbellata*, *Polygonum multiflorum*, *Rubus caesius* fruit, *Benincasa hispida* (*Benincasa hispida* seed), *Capsicum annuum*, *Angelica acutiloba*, *Calendula officinalis*, *Zea mays* or *Zea mays* silk, *Houttuynia cordata*, *Carapichea ipecacuanha*, *Eucommia ulmoides* (*Eucommia ulmoides* leaf), *Solanum lycopersicum*, *Potentilla tormentilla*, *Dioscorea batatas*/*Dioscorea japonica*, *Citrus natsudaidai*, *Zizyphus jujuba* var. *inermis*, *Arachis hypogaea*, *Nandina domestica* (*Nandina domestica* fruit), *Myristica*, *Cinnamomum loureiri*/*Cinnamomum cassia*, *Allium tuberosum*, *Allium sativum*, *Rosa multiflora* (*Rosa multiflora* fruit), *Achillea*, *Rosa multiflora*, *Amygdalus davidiana*, *Cocos nucifera*, *Ananas comosus* fruit, *Ocimum basilicum*, *Nelumbo nucifera* (*Nelumbo nucifera* fruit/seed), *Petroselium crispum*, *Mentha arvensis* var. *piperascens* (*Mentha arvensis* var. *piperascens* leaf), *Coix lacryma-jobi* var. *frumentacea* (*Coix lacryma-jobi* var. *frumentacea* seed), *Musa acuminata*, *Origanum vulgare*, *Vanilla planifolia* beans, *Carica papaya*, *Capsicum annuum* 'grossum', *Hamamelis virginiana* (*Hamamelis virginiana* leaf), *Rosa*, *Belamcanda chinensis*, *Rabdosia japonica* (*Rabdosia japonica* leaf), *Trapa japonica* (*Trapa japonica* fruit), *Chamaecyparis obtusa*, *Ricinus communis*, *Helianthus annus*, *Capsicum annuum*, *Eriobotrya japonica* (*Eriobotrya japonica* leaf), *Areca catechu* (*Areca catechu* peel/nut), *Petasites japonicus*, *Tussilago farfara* (*Tussilago farfara* bud/leaf), *Vitis vinifera* fruit or *Vitis vinifera* peel/seed/leaf, *Fagus crenata*, *Cordyceps sinensis*, *Periandra mediterranea*, *Rubus fruticosus*, *Prunus* fruit, *Vaccinium corymbosum* (*Vaccinium myrtillus*), *Prunus domestica*, *Luffa cylindrica*, *Carthamus tinctorius*, berry fruits, *Bergenia ligulata* (*Bergenia ligulata* root), *Spinacia oleracea*, *Physalis alkekengi* var. *franchetii* (*Physalis alkekengi* var. *franchetii* root), *Tilia miqueliana*, *Paeonia suffruticosa* (*Paeonia suffruticosa* root bark), *Humulus lupulus*, *Simmondsia chinensis*, *Grifola frondosa*, *Ephedra sinica*, *Macadamia integrifolia* nut, *Morus alba* (*Morus alba* root bark/leaf), *Origanum majorana* (*Origanum majorana* leaf), *Morus alba* fruit, *Cydonia oblonga*, *Mangifera indica*, *Garcinia mangostana*, *Citrus reticulata* fruit, *Ganoderma lucidum*, *Mentha spicata*, *Acacia deal-* bata, *Zingilber mioga, Synsepalum dulcificum* fruit, *Sapindus mukurossi, Lithospermum erythrorhizon* (*Lithospermum erythrorhizon* root), Peruvian *Zea mays, Melia azadirachta* (*Melia azadirachta* leaf), *Melissa officinalis, Melilotus officinalis, Cucumis melo* fruit, *Prunus persica* leaf/fruit/kernel, *Vigna radiata, Prunus cerasus* var. *austera* fruit, *Corchorus olitorius, Rodgersia podophylla* (*Centaurea cyanus*), *Monarda fistulosa, Artemisia montana, Eucalyptus globulus, Saxifraga stolonifera, Citrus junos* fruit, *Lilium lancifolium, Rubus idaeus* subsp. *idaeus, Artemisia princeps* (*Artemisia princeps* leaf), *Citrus aurantifolia* fruit, *Secale cereale, Rubus idaeus* leaf/fruit, *Lavandula dentata, Camellia sinensis* (green tea leaf), *Malus domestica* fruit, *Gentiana scabra* var. *buergeri, Citrus limon* fruit, *Cymbopogon citratus, Forsythia suspensa, Astragalus sinicus, Rosmarinus officinalis, Rosa canina, Wasabia japonica*, and *Sanguisorba officinalis*. The plant extract may be incorporated in any of the inner aqueous phase, the oil phase, and the outer aqueous phase, but is particularly preferably incorporated in the outer aqueous phase.

Examples of other beautifying components include *Saccharomyces cerevisae*, hydrolyzed conchiolin, hydrolyzed hyaluronic acid, hydroxypropyltrimonium hyaluronate, and C12-13 alkyl glyceryl hydrolyzed hyaluronate. These components may also be incorporated in any of the inner aqueous phase, the oil phase, and the outer aqueous phase, but is particularly preferably incorporated in the outer aqueous phase.

The contents of the components of the respective phases based on the total amount of the W/O/W emulsion can be determined as appropriate depending on various factors, including the types of an active component(s) and a surfactant, and the type and amount of a solid oil component.

Like the components' contents, the relative ratio of inner aqueous phase/oil phase/outer aqueous phase can also be determined as appropriate depending on the types and amounts of the components to be used. However, for the purpose of maintaining the stability of the emulsion, the weight ratio of the oil phase to the inner aqueous phase is set to lie within the range of 10:90 to 90:10, preferably 20:80 to 80:20, more preferably 25:75 to 75:25. Based on 100 parts by weight of the inner aqueous phase, the oil phase is present in an amount of 10 to 500 parts by weight, preferably 20 to 300 parts by weight, more preferably 50 to 200 parts by weight, and the outer aqueous phase is present in an amount of 50 to 2000 parts by weight, preferably 100 to 1500 parts by weight, more preferably 200 to 1000 parts by weight.

In the present invention, the form of the W/O/W emulsion is not particularly limited as long as the W/O/W emulsion has temporal stability; for example, the droplets of the inner aqueous phase has an average particle size of 0.001 to 100 μm, preferably 0.01 to 100 μm, more preferably 0.1 to 100 μm, and the W/O emulsion has an average particle size of 0.01 to 100 μm, preferably 0.1 to 100 μm, more preferably 0.5 to 100 μm, most preferably 1 to 50 μm.

In the present invention, the W/O/W emulsion preferably has a viscosity at 20-30° C. of 500 to 50,000 mPa·s, more preferably 1,000 to 40,000 mPa·s, still more preferably 2,000 to 30,000 mPa·s. The viscosity is measured by a BM-type viscometer (produced by TOKI SANGYO Co., Ltd.; measurement conditions: using rotor No. 4 at 12 rpm for 1 min.).

Skin Preparation for External Use

As used in the present invention, the term "skin preparation for external use" is a generic name for preparations of such dosage forms that permit application to the skin, including cosmetics such as cream, beauty liquid, milky lotion, toilet lotion, and face pack, quasi-drugs, medicines, and detergents. The applications for which the inventive skin preparation for external use can be used are not particularly limited as long as it is known that emulsions can be applied to these applications, but the inventive skin preparation for external use is preferably used for cosmetics, particularly preferably for cream.

Method for Producing a W/O/W Emulsion

The method for producing a W/O/W emulsion according to the present invention is not particularly limited, and any known method can be used for production, but a W/O/W emulsion having particularly superior temporal stability can be obtained by the following production method.

For example, the W/O/W emulsion can be produced by taking the following two steps: (1) mixing and emulsifying an inner aqueous phase comprising a water soluble active component and an oil phase comprising a solid oil component and a silicone surfactant to thereby prepare a W/O emulsion; and (2) mixing and emulsifying the prepared W/O emulsion and an outer aqueous phase comprising a water soluble polymer.

More specifically, to an oil phase comprising a silicone surfactant, a solid oil component, and any other optional component (e.g., oil soluble active component) is added an inner aqueous phase comprising a water soluble active component and any other optional component (e.g., metal salt), and the mixture is emulsified at a temperature of 50 to 100° C., preferably 65 to 95° C., more preferably 75 to 85° C. to prepare a W/O emulsion. In this process, the inner aqueous phase and the oil phase are mixed at a weight ratio of 10:90 to 90:10, preferably 20:80 to 80:20, more preferably 25:75 to 75:25.

Next, the resulting W/O emulsion is added to an outer aqueous phase comprising an acrylic acid/alkyl methacrylate copolymer, and the mixture is emulsified at a temperature of 70° C. or less, preferably 0 to 60° C., more preferably 10 to 50° C. to thereby prepare a W/O/W emulsion.

EXAMPLES

On the pages that follow, the present invention will be described in detail by way of Examples, but this invention is not limited to these examples.

Example 1

Preparation of W/O/W Emulsions—1

First, various components were mixed at the relative ratio (weight ratio) shown in Table 1 to prepare each of an oil phase, an inner aqueous phase, and an outer aqueous phase. Cetyl PEG/PPG-10/1 dimethicone was used as a silicone surfactant to be incorporated in the oil phase. Next, at a temperature of 80° C., the inner aqueous phase was fed into the oil phase and the mixture was emulsified, whereby a W/O emulsion was prepared. Then, the W/O emulsion was fed into the outer aqueous phase under the condition of 50° C. to obtain a W/O/W emulsion preparation as evaluation sample (1).

In order to compare evaluation sample (1), which is the inventive W/O/W emulsion produced using a silicone surfactant, with samples produced using other surfactants, evaluation samples (2) to (7) were produced using the same components and conditions as in the case of evaluation sample (1), except that the surfactant to be used was varied.

Preparation of W/O/W Emulsions—2

Under the same conditions as in the case of evaluation sample (1) except for the relative component ratios shown in Table 1, there were produced evaluation sample (8), which is related to the inventive W/O/W emulsion comprising a silicone surfactant, as well as evaluation samples (9) to (11), which are comparative examples using not a silicone surfactant but any of different dextrin palmitates as a surfactant.

measurements, using the preparations' appearance and fragrance note as indices. A follow-up evaluation of the preparations' appearance and fragrance note was conducted after 6 months using the following evaluation scale for each index.

(Appearance Evaluation Scale)
○: No change
x: Changed (Resolution occurred)
(Fragrance Note Evaluation Scale)

TABLE 1

Table of components of W/O/W emulsions

| Evaluation sample No. | (1) | (2) | (3) | (4) | (5) | (6) | (7) | (8) | (9) | (10) | (11) |
|---|---|---|---|---|---|---|---|---|---|---|---|
| (Inner aqueous phase) | | | | | | | | | | | |
| Magnesium ascorbyl phosphate (Nikko Chemicals) | 1.0 | 1.0 | 1.0 | 1.0 | 1.0 | 1.0 | 1.0 | 1.0 | 1.0 | 1.0 | 1.0 |
| Purified water | 10.0 | 10.0 | 10.0 | 10.0 | 10.0 | 10.0 | 10.0 | 10.0 | 10.0 | 10.0 | 10.0 |
| Magnesium sulfate | 0.9 | 0.9 | 0.9 | 0.9 | 0.9 | 0.9 | 0.9 | 0.9 | 0.9 | 0.9 | 0.9 |
| (Oil phase) | | | | | | | | | | | |
| Cetyl PEG/PPG-10/1 dimethicone (Evonik Goldschmidt GmbH) | 10.0 | | | | | | | | | | |
| Polyglyceryl oleate | | 10.0 | | | | | | | | | |
| Polyglyceryl pentaoleate | | | 10.0 | | | | | | | | |
| Polyglycelyl pentahydroxystearate | | | | 10.0 | | | | | | | |
| Sorbitan oleate | | | | | 10.0 | | | | | | |
| Polyoxyethylene hydrogenated castor oil | | | | | | 10.0 | | | | | |
| Polyglycerol polyricinoleate | | | | | | | 10.0 | | | | |
| Cetyl PEG/PPG-10/1 dimethicone | | | | | | | | 5.0 | | | |
| Dextrin palmitate (Rheopearl TL2; Chiba Flour Milling) | | | | | | | | | 5.0 | | |
| Dextrin palmitate (Rheopearl KL2; Chiba Flour Milling) | | | | | | | | | | 5.0 | |
| Dextrin palmitate/dextrin octanoate (Rheopearl TT2; Chiba Flour Milling) | | | | | | | | | | | 5.0 |
| Liquid paraffin | 19.1 | 19.1 | 19.1 | 19.1 | 19.1 | 19.1 | 19.1 | 24.1 | 24.1 | 24.1 | 24.1 |
| Squalane | 2.0 | 2.0 | 2.0 | 2.0 | 2.0 | 2.0 | 2.0 | 2.0 | 2.0 | 2.0 | 2.0 |
| Microcrystalline wax (Nikko Rica) | 0.9 | 0.9 | 0.9 | 0.9 | 0.9 | 0.9 | 0.9 | 0.9 | 0.9 | 0.9 | 0.9 |
| Tocopherol acetate | 1.0 | 1.0 | 1.0 | 1.0 | 1.0 | 1.0 | 1.0 | 1.0 | 1.0 | 1.0 | 1.0 |
| (Outer aqueous phase) | | | | | | | | | | | |
| Acrylates/alkyl acrylate crosspolymer (Nikko Chemicals) | 0.1 | 0.1 | 0.1 | 0.1 | 0.1 | 0.1 | 0.1 | 0.1 | 0.1 | 0.1 | 0.1 |
| Sodium hydroxide | 0.1 | 0.1 | 0.1 | 0.1 | 0.1 | 0.1 | 0.1 | 0.1 | 0.1 | 0.1 | 0.1 |
| Methylparaben | 0.1 | 0.1 | 0.1 | 0.1 | 0.1 | 0.1 | 0.1 | 0.1 | 0.1 | 0.1 | 0.1 |
| 1,3-butyleneglycol | 16.1 | 16.1 | 16.1 | 16.1 | 16.1 | 16.1 | 16.1 | 16.1 | 16.1 | 16.1 | 16.1 |
| Concentrated glycerin | 5.0 | 5.0 | 5.0 | 5.0 | 5.0 | 5.0 | 5.0 | 5.0 | 5.0 | 5.0 | 5.0 |
| Polyoxyethylene sorbitan monooleate (20E.O.) (Kao) | 5.0 | 5.0 | 5.0 | 5.0 | 5.0 | 5.0 | 5.0 | 5.0 | 5.0 | 5.0 | 5.0 |
| Purified water | bal | bal | bal | bal | bal | bal | bal | bal | bal | bal | bal |

<Evaluation of the Structure of the W/O/W Emulsion>

Figure 2:
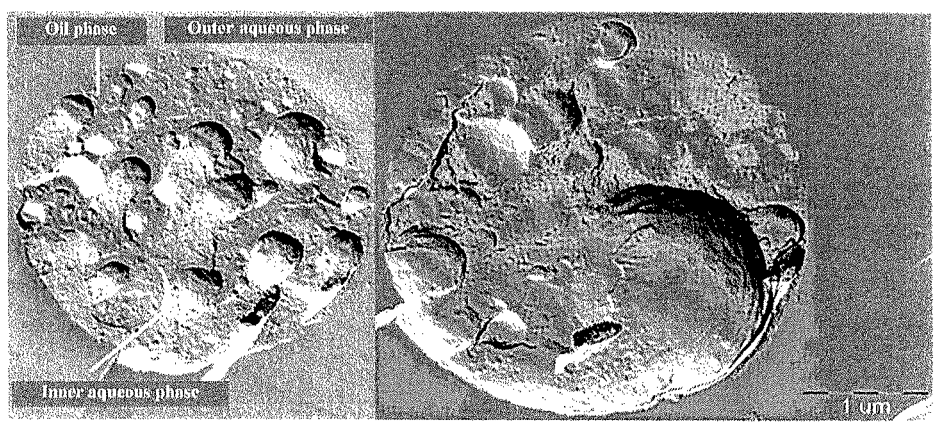
FIG. 2 shows a transmission electron microphotograph (TEM) of W/O/W emulsion (1) which is an embodiment of this invention.

FIGS. 1 and 2 show microphotographs of the inventive W/O/W emulsion (evaluation sample (1)) obtained by the above-mentioned method. From these microphotographs shown in FIGS. 1 and 2, it was confirmed that the W/O/W emulsion composed of the inner aqueous phase, the oil phase, and the outer aqueous phase was formed successfully.

Figure 3:
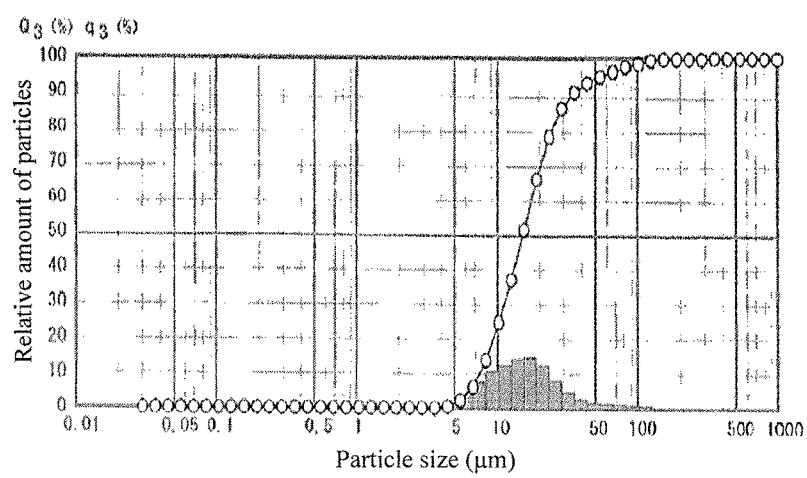
FIG. 3 shows the particle size distribution of a WO emulsion contained in a W/O/W emulsion which is an embodiment of this invention.

Also, W/O emulsion droplets contained in the W/O/W emulsion were each measured for particle size on the basis of these microphotographs, and the obtained particle size distribution is shown in FIG. 3. From the results in FIG. 3, it was confirmed that droplets having a single-peak particle size distribution were formed successfully. The W/O emulsion had an average particle size of 10 to 20 μm.

<Stability Evaluation of W/O/W Emulsions: Investigation of Surfactants>

Confirmation of the stability of the produced emulsion preparations was made under the acceleration conditions of 40° C. and 75% RH on the basis of the particle size ○: No change
x: Changed (A smell of oxidized oil or the base was detected.)

Table 2 shows the results of the investigation of the temporal stability of the preparations produced using different surfactants. As is evident from this table, evaluation samples (2) to (7), which were produced as comparative examples using other surfactants than the silicone surfactant, did not provide stable W/O/W emulsions. It is particularly worth noting that evaluation samples (9) to (11), which were also produced as comparative examples using dextrin palmitates with different degrees of substitution, did not provide stable W/O/W emulsions, in spite of the fact that they used different dextrin fatty acid esters in combination with the water soluble polymer and the solid oil component. From these results, it was confirmed that a W/O/W emulsion is stabilized by incorporating not only a silicone surfactant but also a water soluble polymer and a solid oil component.

TABLE 2

Temporal stability of the W/O/W emulsions
produced using different surfactants

| | Evaluation sample No. | | | | | | | | | | |
|---|---|---|---|---|---|---|---|---|---|---|---|
| | (1) | (2) | (3) | (4) | (5) | (6) | (7) | (8) | (9) | (10) | (11) |
| | | | | | (Stability) | | | | | | |
| Appearance | ○ | X | X | X | X | X | X | ○ | X | X | X |
| Fragrance note | ○ | X | X | X | X | X | X | ○ | X | X | X |

Figure 4:
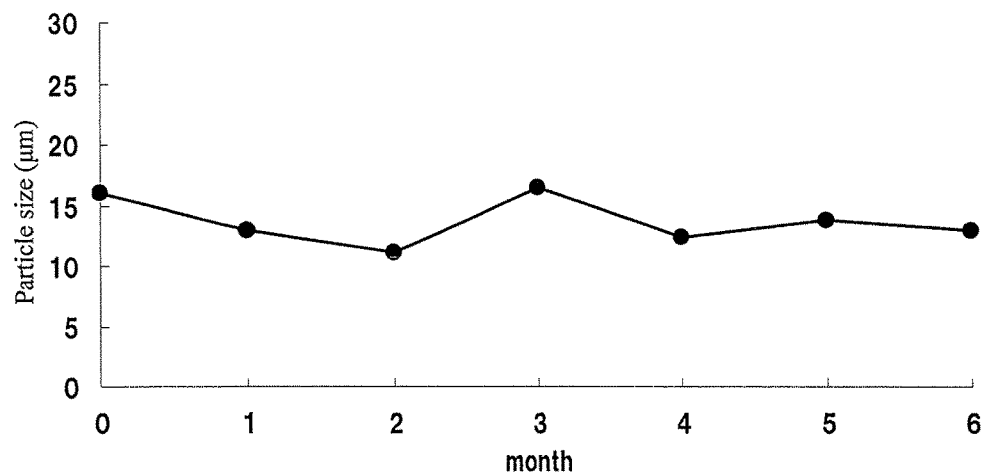
FIG. 4 shows the change with time in the particle size of a W/O emulsion contained in a W/O/W emulsion produced using a silicone surfactant, which is an embodiment of this invention.

FIG. 4 shows the change in the particle size of evaluation sample (1) which is the W/O/W emulsion produced using the silicone surfactant. As is evident from FIG. 4, the W/O/W emulsion as evaluation sample (1) showed no change in particle size after 6 months, which demonstrates that this emulsion maintained its stability. In other words, the results in this figure show that the W/O/W emulsion of the present invention was extremely stable because the W/O emulsion contained therein maintained their particle size at a fixed level for 6 months or more. The results also suggest that there occurred no defects such as coalescence of W/O emulsion droplets contained in the inventive W/O/W emulsion, or of inner aqueous phase droplets contained in said W/O emulsion. This demonstrates that the W/O/W emulsion of this invention has sufficient temporal stability to be used as a technique for formulating cosmetics.

<Permeability Test Using a Cultured Skin Model>
(Evaluation Method)

In order to confirm the permeability of the produced W/O/W emulsion (evaluation sample (1)), permeability test was conducted using a cultured skin model. The comparative sample used was an O/W emulsion produced using the same materials as those of evaluation sample (1).

Two milliliters of PBS was added to each well of a 12-well plate, and EpiSkin™ Large Model, a three-dimensional cultured epidermis model, was mounted on each well. Either of the samples was applied to the stratum corneum side of each of the skin models, and incubation was started at 37° C. Six hours after the application of the samples, the skin models and receiver solutions were collected, and tocopherol acetate was quantified by HPLC. The skin models after undergoing the test were each placed in a microtube containing 1 mL of ethanol and crushed using a Tissue Lyser. Then, 0.1 mL each of the supernatants was collected for use in tocopherol acetate measurement.

(Evaluation Results)

Figure 5:
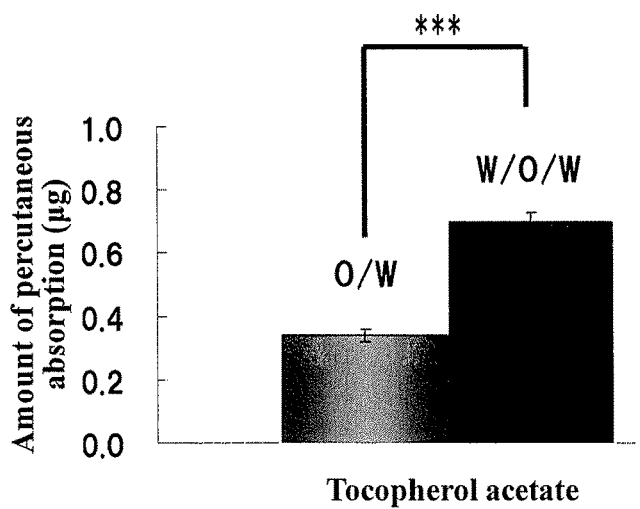
FIG. 5 shows the results of the comparative permeability test conducted for a W/O/W emulsion, which is an embodiment of this invention, and a conventional O/W emulsion, using a cultured skin model.

FIG. 5 shows the results of the permeability test. As is evident from the results in this figure, the percutaneous absorbability of the active component (tocopherol acetate) incorporated in the oil phase of the W/O/W emulsion was significantly improved as compared with the case of the O/W emulsion. Since the results suggest that the water soluble active component present in the inner aqueous phase dispersed in the oil phase would also be absorbed at the same time, the percutaneous absorbability of the inner aqueous phase component is also presumed to be improved in the same manner by using the W/O/W emulsion of the present invention.

Example 2

Stability Evaluation of W/O/W Emulsions

Investigation of Solid Oil Component Content

FIG. 3 shows the results of the comparative investigation of the stability of W/O/W emulsions produced using varied amounts of a solid oil component (microcrystalline wax). Evaluation samples (12) to (16) were prepared using the same conditions as in the case of evaluation sample (1) of Example 1, except for using varied amounts of microcrystalline wax. And they were evaluated for the stability of the emulsion preparations by the same method as the stability evaluation method of Example 1, using the preparations' appearance and fragrance note as indices.

As shown in Table 3, it was found that no stable W/O/W emulsions can be obtained if the wax is used only in a relatively low amount. In other words, it was confirmed that increasing the viscosity of an oil phase using a wax allows a W/O emulsion contained in an outer aqueous phase to be kept stable, contributing greatly to the stability of a W/O/W emulsion.

TABLE 3

Comparison of microcrystalline wax contents

| Evaluation sample No. | (12) | (13) | (14) | (15) | (16) |
|---|---|---|---|---|---|
| (Inner aqueous phase) | | | | | |
| Magnesium ascorbyl phosphate | 1.0 | 1.0 | 1.0 | 1.0 | 1.0 |
| Purified water | 10.0 | 10.0 | 10.0 | 10.0 | 10.0 |
| Magnesium sulfate | 0.9 | 0.9 | 0.9 | 0.9 | 0.9 |
| (Oil phase) | | | | | |
| Cetyl PEG/PPG-10/1 dimethicone | 10.0 | 10.0 | 10.0 | 10.0 | 10.0 |
| Liquid paraffin | 19.1 | 19.1 | 19.1 | 19.1 | 19.1 |
| Squalane | 2.0 | 2.0 | 2.0 | 2.0 | 2.0 |
| Microcrystalline wax | 0 | 0.3 | 0.6 | 0.9 | 1.2 |
| Tocopherol acetate | 1.0 | 1.0 | 1.0 | 1.0 | 1.0 |
| (Outer aqueous phase) | | | | | |
| Acrylates/alkyl acrylate crosspolymer | 0.1 | 0.1 | 0.1 | 0.1 | 0.1 |
| Sodium hydroxide | 0.1 | 0.1 | 0.1 | 0.1 | 0.1 |
| Methylparaben | 0.1 | 0.1 | 0.1 | 0.1 | 0.1 |
| 1,3-butylene glycol | 16.1 | 16.1 | 16.1 | 16.1 | 16.1 |
| Concentrated glycerin | 5.0 | 5.0 | 5.0 | 5.0 | 5.0 |
| Polyoxyethylene sorbitan monooleate (20E.O.) | 5.0 | 5.0 | 5.0 | 5.0 | 5.0 |
| Purified water | bal | bal | bal | bal | bal |
| (Stability) | | | | | |
| Appearance | X | X | X | ○ | ○ |
| Fragrance note | X | X | X | ○ | ○ |

Example 3

Stability Evaluation of W/O/W Emulsions

Investigation of Water Soluble Polymers

Comparative investigation was made of whether a water soluble polymer incorporated in an outer aqueous phase contributes to the stability of a W/O/W emulsion. Evaluation sample (17) was prepared using the same conditions as in the case of evaluation sample (1) of Example 1, except for using purified water in place of an acrylates/alkyl acrylate crosspolymer. Further investigation was made of whether even a W/O/W emulsion produced using a different type of water soluble polymer is capable of maintaining its stability. Evaluation sample (18) was prepared using the same conditions as in the case of evaluation sample (1) of Example 1, except for using xanthan gum in place of an acrylates/alkyl acrylate crosspolymer. The prepared evaluation samples were evaluated for the stability of the emulsion preparations by the same method as the stability evaluation method of Example 1, using the preparations' appearance and fragrance note as indices, except that the evaluation was conducted one month after the preparation of the emulsions.

As shown in Table 4, the appearance and fragrance note of evaluation sample (17) were both evaluated as "x" (changed), which indicates that no stable W/O/W emulsion can be obtained without incorporating a water soluble polymer in an outer aqueous phase. On the other hand, the appearance and fragrance note of evaluation sample (18) were both evaluated as "◯" (no change), which demonstrates that a stable W/O/W emulsion can be obtained even if xanthan gum is used as a water soluble polymer. These results suggest that a water soluble polymer would increase the viscosity of an outer aqueous phase to decrease the flowability of a W/O emulsion, thereby effectively reducing the flocculation of W/O emulsion droplets and contributing greatly to the stability of a W/O/W emulsion.

TABLE 4

Comparisons of the types of water soluble polymers, and of the presence and absence of a water soluble polymer

| Evaluation sample No. | (1) | (17) | (18) |
|---|---|---|---|
| (Inner aqueous phase) | | | |
| Magnesium ascorbyl phosphate | 1.0 | 1.0 | 1.0 |
| Purified water | 10.0 | 10.0 | 10.0 |
| Magnesium sulfate | 0.9 | 0.9 | 0.9 |
| (Oil phase) | | | |
| Cetyl PEG/PPG-10/1 dimethicone | 10.0 | 10.0 | 10.0 |
| Liquid paraffin | 19.1 | 19.1 | 19.1 |
| Squalane | 2.0 | 2.0 | 2.0 |
| Microcrystalline wax | 0.9 | 0.9 | 0.9 |
| Tocopherol acetate | 1.0 | 1.0 | 1.0 |
| (Outer aqueous phase) | | | |
| Acrylates/alkyl acrylate crosspolymer (2% aq) | 5.0 | 0 | |
| Xanthan gum (2% aq) (NOMCORT Z; the Nisshin Oillio Group) | | 0 | 5.0 |
| Sodium hydroxide (10% aq) | 1.0 | 1.0 | 1.0 |
| Methylparaben | 0.1 | 0.1 | 0.1 |
| 1,3-butylene glycol | 16.1 | 16.1 | 16.1 |
| Glycerol | 5.0 | 5.0 | 5.0 |
| Polyoxyethylene sorbitan monooleate (20 E.O.) | 5.0 | 5.0 | 5.0 |
| Purified water | bal | bal | bal |
| (Stability) | | | |
| Appearance | ◯ | X | ◯ |
| Fragrance note | ◯ | X | ◯ |

Example 4

Stability Evaluation of W/O/W Emulsions

Investigation of Silicone Surfactants

Comparative evaluation was made of whether the type of a silicone surfactant influences the stability of a W/O/W emulsion. Evaluation sample (19) was prepared using the same conditions as in the case of evaluation sample (1) of Example 1, except that the type of a silicone surfactant was changed. The silicone surfactant used to prepare evaluation sample (19) was lauryl PEG-9 polydimethylsiloxyethyl dimethicone, which is a silicone surfactant having a polyether group and an alkyl group, like the one used in evaluation sample (1). The prepared evaluation samples were evaluated for the stability of the emulsion preparations by the same method as the stability evaluation method of Example 1, using the preparations' appearance and fragrance note as indices, except that the evaluation was conducted one month after the preparation of the emulsions.

As shown in Table 5, the appearance and fragrance note of evaluation sample (19) were both evaluated as "◯" (no change), which demonstrates that a stable W/O/W emulsion can be obtained particularly in the case where among silicone surfactants, the one having a polyether group and an alkyl group is used. The silicone surfactants used for the evaluation, i.e., cetyl PEG/PPG-10/1 dimethicone and lauryl PEG-9 polydimethylsiloxyethyl dimethicone, had a HLB of about 5.0 and about 3.0, respectively.

TABLE 5

Comparison of the types of silicone surfactants

| Evaluation sample No. | (1) | (19) |
|---|---|---|
| (Inner aqueous phase) | | |
| Magnesium ascorbyl phosphate | 1.0 | 1.0 |
| Purified water | 10.0 | 10.0 |
| Magnesium sulfate | 0.9 | 0.9 |
| (Oil phase) | | |
| Cetyl PEG/PPG-10/1 dimethicone | 10.0 | |
| Lauryl PEG-9 polydimethylsiloxyethyl dimethicone (KF-6038; Shin-Etsu Chemical) | | 10.0 |
| Liquid paraffin | 19.1 | 19.1 |
| Squalane | 2.0 | 2.0 |
| Microcrystalline wax | 0.9 | 0.9 |
| Tocopherol acetate | 1.0 | 1.0 |
| (Outer aqueous phase) | | |
| Acrylates/alkyl acrylate crosspolymer (2% aq) | | 5.0 |
| Sodium hydroxide (10% aq) | 1.0 | 1.0 |
| Methylparaben | 0.1 | 0.1 |
| 1,3-butylene glycol | 16.1 | 16.1 |
| Glycerol | 5.0 | 5.0 |
| Polyoxyethylene sorbitan monooleate (20 E.O.) | 5.0 | 5.0 |
| Purified water | bal | bal |
| (Stability) | | |
| Appearance | ◯ | ◯ |
| Fragrance note | ◯ | ◯ |

Production Example 1

Functional Cream

Table 6 shows the relative ratio of the materials used to produce a functional cream.

First, the inner aqueous phase components ((6), (7)) were dissolved, and then the oil phase components ((1) to (5)) were fed and the mixture was emulsified at a temperature of about 80° C. to give a W/O emulsion. The resulting W/O emulsion was mixed with an outer aqueous phase which had been obtained by dispersing and dissolving the outer aqueous phase components ((8) to (16)) in part of purified water (17), whereby a W/O/W emulsion was obtained.

The resulting cream was filled in a container with a cap, stored at 25° C. with the container being closed with the cap, and evaluated for stability under the same conditions as in the case of the above-mentioned stability evaluation of the emulsions prepared in Example 1. No change had been found in the appearance or fragrance note of the cream for 3 months, and this demonstrates that the functional cream has temporal stability.

TABLE 6

| | Components | Relative ratio |
|---|---|---|
| (1) | Cetyl PEG/PPG-10/1 dimethicone | 5 |
| (2) | Liquid paraffin | 24.15 |
| (3) | Squalane | 2 |
| (4) | Microcrystalline wax | 0.9 |
| (5) | Tocopherol acetate | 0.05 |
| (6) | Magnesium ascorbyl phosphate | 1 |
| (7) | Magnesium sulfate | 0.9 |
| (8) | Acrylates/alkyl acrylate crosspolymer | 0.2 |
| (9) | Sodium hydroxide | 0.1 |
| (10) | Methylparaben | 0.1 |
| (11) | 1,3-butylene glycol | 8 |
| (12) | Glycerol | 5 |
| (13) | Polyoxyethylene sorbitan monooleate (20 E.O.) | 5 |
| (14) | Magnesium ascorbyl phosphate | 2 |
| (15) | Plant extract | balance |
| (16) | Perfume | 0.1 |
| (17) | Purified water | balance |

INDUSTRIAL APPLICABILITY

The present invention can provide a W/O/W emulsion having temporal stability which comprises a water soluble active component in an inner aqueous phase, and a method for producing the same. The W/O/W emulsion and method of this invention can be applied to techniques for formulating cosmetics having various functions including skin-lightening effect.

The invention claimed is:

1. A W/O/W emulsion comprising a water soluble active component in an inner aqueous phase,
wherein the W/O/W emulsion comprises: a solid oil component and a silicone surfactant in an oil phase; and a water soluble polymer and polyoxyethylene sorbitan monooleate in an outer aqueous phase,
wherein the solid oil component is microcrystalline wax, and
wherein the silicone surfactant has a polyether group and an alkyl group, and wherein the W/O/W emulsion has a viscosity of 2,000 to 30,000 mPa·s at 20-30° C. measured with a BM-type viscometer using rotor No. 4 at 12 rpm for 1 min.

2. The W/O/W emulsion according to claim 1, wherein the silicone surfactant having a polyether group and an alkyl group is lauryl PEG-9 polydimethylsiloxyethyl dimethicone or cetyl PEG/PPG-10/1 dimethicone.

3. The W/O/W emulsion according to claim 1, wherein a HLB value of the silicone surfactant is 7 or less.

4. The W/O/W emulsion according to claim 1, wherein the water soluble polymer is an acrylic acid/alkyl methacrylate copolymer or xanthan gum.

5. The W/O/W emulsion according to claim 1, further comprising a metal salt in the inner aqueous phase.

6. The W/O/W emulsion according to claim 1, wherein the water soluble active component is an ascorbic acid derivative.

7. The W/O/W emulsion according to claim 1, wherein the weight ratio of the inner aqueous phase to the oil phase is in the range of 10:90 to 90:10.

8. The W/O/W emulsion according to claim 1, further comprising an oil soluble active component in the oil phase.

9. The W/O/W emulsion according to claim 8, wherein the oil soluble active component is a tocopherol derivative.

10. The W/O/W emulsion according to claim 1, wherein the W/O/W emulsion is a skin preparation for external use.

11. A method for producing a W/O/W emulsion, comprising the steps of:
mixing and emulsifying an inner aqueous phase comprising a water soluble active component and an oil phase comprising a solid oil component and a silicone surfactant to thereby prepare a W/O emulsion; and
mixing and emulsifying the prepared W/O emulsion and an outer aqueous phase comprising a water soluble polymer and polyoxyethylene sorbitan monooleate,
wherein the solid oil component is microcrystalline wax, and
wherein the silicone surfactant has a polyether group and an alkyl group, and wherein the W/O/W emulsion has a viscosity of 2,000 to 30,000 mPa·s at 20-30° C. measured with a BM-type viscometer using rotor No. 4 at 12 rpm for 1 min.

12. The method for producing a W/O/W emulsion according to claim 11, wherein the inner aqueous phase and the oil phase are mixed at a weight ratio of 10:90 to 90:10.

13. The method for producing a W/O/W emulsion according to claim 11, wherein the silicone surfactant having a polyether group and an alkyl group is lauryl PEG-9 polydimethylsiloxyethyl dimethicone or cetyl PEG/PPG-10/1 dimethicone.

14. The method for producing a W/O/W emulsion according to claim 11, wherein the water soluble polymer is an acrylic acid/alkyl methacrylate copolymer or xanthan gum.

15. The method for producing a W/O/W emulsion according to claim 11, further comprising a metal salt in the inner aqueous phase.

* * * * *